(12) United States Patent
Merillat et al.

(10) Patent No.: US 12,397,273 B2
(45) Date of Patent: Aug. 26, 2025

(54) TATTOO INK MIXING APPARATUS

(71) Applicant: The Original Mixing Cartridge LLC, Wauseon, OH (US)

(72) Inventors: Albert Merillat, Wauseon, OH (US); Ryan Gipperich, Wauseon, OH (US)

(73) Assignee: The Original Mixing Cartridge LLC, Wauseon, OH (US)

( * ) Notice: Subject to any disclaimer, the term of this patent is extended or adjusted under 35 U.S.C. 154(b) by 611 days.

(21) Appl. No.: 17/878,261

(22) Filed: Aug. 1, 2022

(65) Prior Publication Data

US 2022/0370971 A1 Nov. 24, 2022

Related U.S. Application Data

(63) Continuation of application No. 16/782,701, filed on Feb. 5, 2020, now Pat. No. 11,400,425.

(60) Provisional application No. 62/801,233, filed on Feb. 5, 2019.

(51) Int. Cl.
| | | |
|---|---|---|
| *B01F 31/65* | (2022.01) | |
| *A61M 37/00* | (2006.01) | |
| *B01F 31/44* | (2022.01) | |
| *B01F 31/445* | (2022.01) | |
| *B05B 7/04* | (2006.01) | |
| *B01F 31/00* | (2022.01) | |
| *B01F 101/21* | (2022.01) | |
| *B01F 101/35* | (2022.01) | |

(52) U.S. Cl.
CPC ....... *B01F 31/651* (2022.01); *A61M 37/0084* (2013.01); *B01F 31/443* (2022.01); *B01F 31/445* (2022.01); *B05B 7/0408* (2013.01); *A61M 2205/071* (2013.01); *B01F 31/70* (2022.01); *B01F 2101/21* (2022.01); *B01F 2101/35* (2022.01)

(58) Field of Classification Search
CPC ........... A61M 37/0076; A61M 37/0084; B01F 31/651
See application file for complete search history.

(56) References Cited

U.S. PATENT DOCUMENTS

| | | |
|---|---|---|
| 3,195,778 A | 7/1965 | Coates |
| 3,322,121 A | 5/1967 | Banker |
| 4,671,277 A | 6/1987 | Beuchat |
| 4,776,704 A | 10/1988 | Kopunek et al. |
| 4,798,582 A * | 1/1989 | Sarath .................. B43K 1/003 604/47 |

(Continued)

FOREIGN PATENT DOCUMENTS

| | | |
|---|---|---|
| EP | 2206530 | 7/2010 |
| WO | WO201108004 | 1/2011 |

(Continued)

*Primary Examiner* — Elizabeth Insler
(74) *Attorney, Agent, or Firm* — MacMillan, Sobanski & Todd, LLC

(57) ABSTRACT

A tattoo ink mixing apparatus has a housing having a cavity, a plunger movable between a first position and a second position, and a dynamic member disposed in the cavity and adapted to engage with the plunger distal end. The dynamic member moves in response to movement of the plunger and alternatively creates a suction force and an expulsion force in the opening of the distal end of the housing as the plunger moves between its first and second positions.

20 Claims, 9 Drawing Sheets

(56) References Cited

U.S. PATENT DOCUMENTS

| | | |
|---|---|---|
| 5,054,339 A | 10/1991 | Yacowitz |
| 6,345,553 B1 | 2/2002 | Adler et al. |
| 6,505,530 B2 | 1/2003 | Adler et al. |
| 7,380,480 B1 | 6/2008 | Chen |
| 7,470,237 B2 * | 12/2008 | Beckman ............ A61B 10/0275 600/564 |
| 8,356,927 B1 | 1/2013 | Lordi et al. |
| 8,794,109 B2 | 8/2014 | Lee |
| 9,044,582 B2 * | 6/2015 | Chang .................. A61M 37/00 |
| 9,050,445 B2 | 6/2015 | Klebs et al. |
| D745,152 S | 12/2015 | Mayer |
| D746,455 S | 12/2015 | Mayer |
| 9,393,395 B2 | 7/2016 | Miller et al. |
| 9,636,491 B1 | 5/2017 | O'Brien, III |
| 9,833,602 B2 | 12/2017 | Norman |
| 10,052,469 B2 | 8/2018 | Chan et al. |
| 10,610,327 B2 | 4/2020 | Niven et al. |
| 11,020,203 B2 | 6/2021 | Niven et al. |
| 11,040,185 B2 | 6/2021 | Johansson |
| 11,052,232 B2 | 7/2021 | Xiao |
| 2003/0171767 A1 | 9/2003 | Koplen |
| 2006/0020283 A1 | 1/2006 | Lisec |
| 2010/0036317 A1 | 2/2010 | Oginski et al. |
| 2010/0206138 A1 | 8/2010 | Clark |
| 2012/0163117 A1 | 6/2012 | Guidry, Jr. et al. |
| 2013/0226211 A1 | 8/2013 | Xiao |
| 2015/0151098 A1 | 6/2015 | Spendlove et al. |
| 2015/0352346 A1 | 12/2015 | Webb |
| 2016/0184572 A1 * | 6/2016 | Xiao .................. A61M 37/0076 606/186 |
| 2016/0184573 A1 | 6/2016 | Brookshire et al. |
| 2016/0354592 A1 | 12/2016 | Juan |
| 2017/0072178 A1 | 3/2017 | Xiao |
| 2018/0050858 A1 | 2/2018 | May et al. |
| 2018/0050859 A1 | 2/2018 | May et al. |
| 2018/0056054 A1 | 3/2018 | Siciliano |
| 2018/0065776 A1 | 3/2018 | May et al. |
| 2018/0065783 A1 | 3/2018 | May et al. |
| 2018/0126342 A1 | 5/2018 | Kent |
| 2019/0217072 A1 | 7/2019 | Xiao |
| 2020/0222147 A1 | 7/2020 | Niven et al. |
| 2020/0324258 A1 | 10/2020 | Merillat et al. |
| 2020/0352620 A1 | 11/2020 | Winkelman et al. |
| 2021/0244496 A1 | 8/2021 | Niven et al. |
| 2021/0299423 A1 | 9/2021 | Simeone et al. |
| 2021/0308440 A1 | 10/2021 | Bordeaux et al. |

FOREIGN PATENT DOCUMENTS

| | | |
|---|---|---|
| WO | WO2015160370 | 10/2015 |
| WO | WO2017178069 | 10/2017 |
| WO | 2020106175 A1 | 5/2020 |

* cited by examiner

TATTOO INK MIXING APPARATUS

CROSS-REFERENCE TO RELATED APPLICATION

This application is a continuation of U.S. patent application Ser. No. 16/782,701, filed Feb. 5, 2020 and issued as U.S. Pat. No. 11,400,425 on Aug. 2, 2022, which claims the benefit of U.S. Provisional Application No. 62/801,233, filed Feb. 5, 2019. The entire disclosure of each of these related applications is hereby incorporated by reference into this disclosure.

FIELD

The disclosure relates generally to the field of tattoos. More specifically, the disclosure relates to tattoo ink mixing apparatuses and tattoo machine systems useful for mixing tattoo ink. Particular embodiments relate to tattoo ink mixing cartridges that utilize a tattoo machine's axial motion to mix tattoo ink.

BACKGROUND

A need exists for tattoo ink mixing apparatuses, tattoo ink mixing cartridges to be used with tattoo machines, and tattoo machine systems.

DETAILED DESCRIPTION

The following detailed description and the appended drawings describe and illustrate various example embodiments of tattoo ink mixing apparatuses and tattoo machine system. The description and illustration of these examples are provided to enable one skilled in the art to make and use a tattoo ink mixing apparatus. They are not intended to limit the scope of the claims in any manner.

Figure 1:
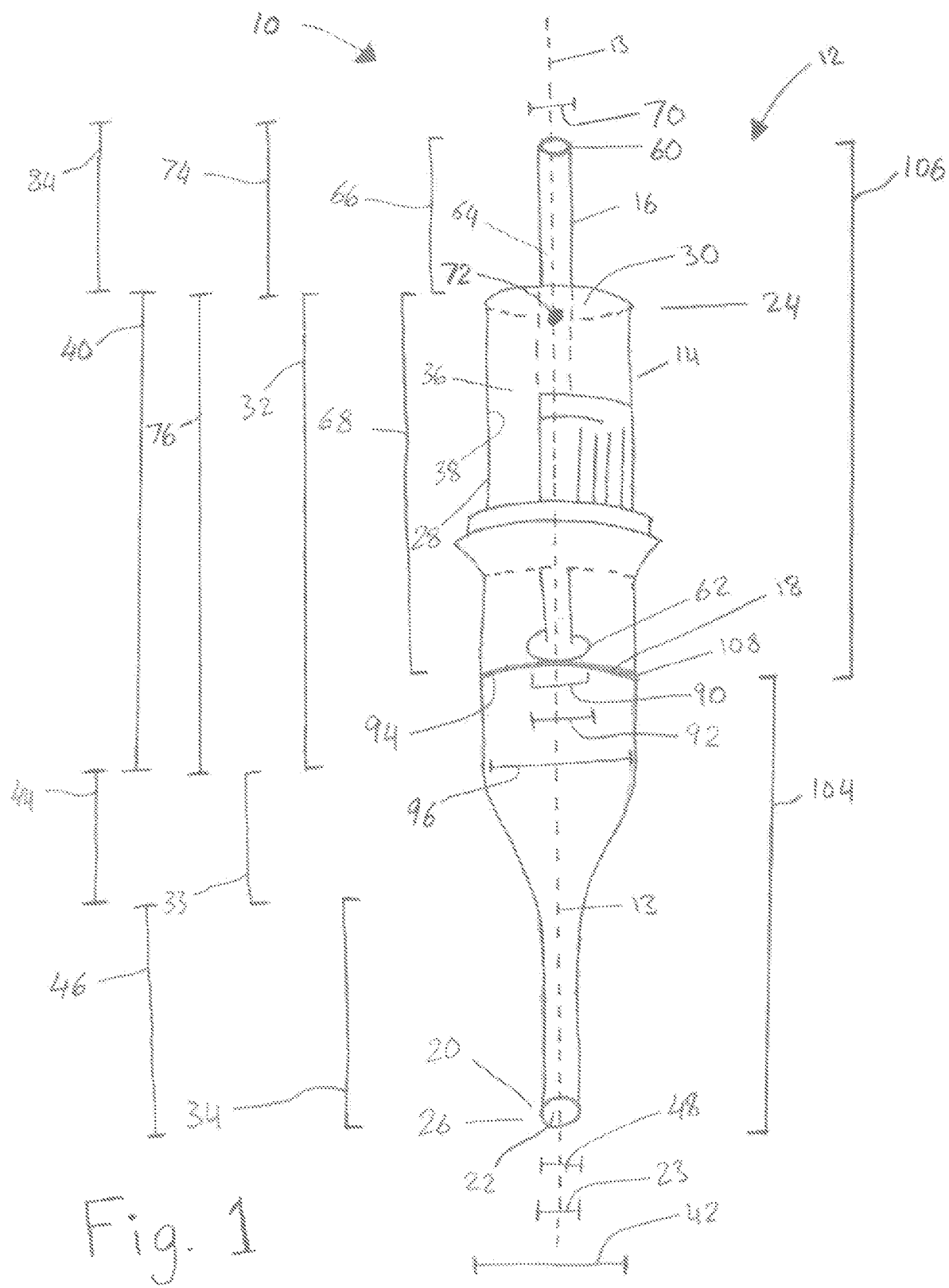
FIG. 1 is a perspective view of an example tattoo ink mixing apparatus according to one embodiment.

FIG. 1 illustrates an example embodiment of a tattoo ink mixing apparatus 10. The tattoo ink mixing apparatus 10 comprises a cartridge 12 having a lengthwise axis 13, a cartridge housing 14, a plunger 16, a dynamic member 18, and a cartridge distal end 20 defining an opening 22.

The cartridge housing 14 comprises a housing proximal end 24, a housing distal end 26, and a housing body 28 extending from the housing proximal end 24 to the housing distal end 26. The housing proximal end 24 defines a housing proximal end opening 30 that provides access to a cavity 36 located within the housing body 28. The housing body 28 defines an inside wall 38, a housing proximal portion 32, an intermediate portion 33, and a housing distal portion 34. The housing proximal portion 32 extends from the housing proximal end 24 to the housing intermediate portion 33 and has a first length 40. The housing intermediate portion 33 tapers from the housing proximal portion 32 to the housing distal portion 34 and has a second length 44. The housing distal portion 34 extends from the housing intermediate portion 33 to the housing distal end 26 and has a third length 46. In the illustrated embodiment, the first length 40 is greater than each of the second length 44 and the third length 46.

The housing proximal portion 32 has a first diameter 42 and the housing distal portion 34 has a second diameter 48. In the illustrated embodiment, the first diameter 42 is greater than the second diameter 48.

While the housing body 28 has been illustrated as having an intermediate portion that tapers from the proximal portion to the distal portion, the tapered intermediate portion can be omitted and the housing body can comprise a single portion. Alternatively, the housing body can have multiple tapered intermediate portions and skilled artisans will be able to select an appropriate number of tapered intermediate portions based on various considerations. Example number of tapered intermediate portions that are considered suitable include one, more than one, a plurality, two, three, or any other number considered suitable for a particular embodiment.

While the housing proximal portion 32 has been illustrated as having a first length 40 that is greater than each of the second length 44 of housing intermediate portion 33 and the third length 46 of housing distal portion 34, and a first diameter 42 that is greater than the second diameter 48 of housing distal portion 34, any suitable lengths and diameters can be used and a skilled artisan will be able to select an appropriate first length, second length, third length, first diameter, and second diameter based on various considerations. Example lengths considered suitable for a first, second, and third lengths include a first length that is equal to, substantially equal to, or less than each of the second length and the third length. Example diameters considered suitable for a first and second diameters include a first diameter that is equal to, substantially equal to, greater than, or less than the second diameter.

The housing body 28 defines the cavity 36 that has a cavity mixing chamber 104 and a cavity proximal chamber 106. He cavity mixing chamber 104 extends from a first location 108 between the housing proximal end 24 and the housing distal end 26 to the opening 22 defined on the cartridge distal end 20. The opening 22 provides direct access to the cavity mixing chamber 104. The cavity proximal chamber 106 extends from the opening 30 defined on the housing proximal end 24 to the first location 108. The opening 30 provides direct access to the cavity proximal chamber 106. The cavity proximal chamber 106 is adapted to receive the distal end 62 and the second portion 68 of the plunger 16 such that the distal end 62 and the second portion 68 of the plunger 16 are disposed in the cavity proximal chamber 106.

Opening 30 has a diameter 31 that is equal to the first diameter 42 of housing proximal portion 32. Each of openings 22 and 30 provides direct access to the cavity 36 such that any material disposed through either of openings 22 and 30 is disposed in the cavity 36. Each of opening 30 and opening 22 can have any suitable shape and size and skilled artisans will be able to select an appropriate shape and size for the openings based on various considerations. Example shapes considered suitable for the openings include round, oval, and any other shapes considered suitable for a particular embodiment.

Plunger 16 comprises a proximal end 60, a distal end 62, an elongate body 64, a first portion 66, and a second portion 68. Elongate body 64 extends from the proximal end 60 to the distal end 62 and has a plunger diameter 70. In the illustrated embodiment, plunger diameter 70 is substantially less than the first diameter of the proximal portion 40 of the housing body 28. Skilled artisans will be able to select an appropriate plunger diameter based on various considerations.

The plunger first portion 66 extends from the plunger proximal end 60 to a center point 72 located between the plunger proximal end 60 and the plunger distal end 62 and has a first length 74 measured along the lengthwise axis 13. The plunger second portion 68 extends from the center point 72 to the plunger distal end 62 and has a second length 76 measured along the lengthwise axis 13. In the illustrated embodiment, the center point 72 lies halfway between the proximal end 60 and the distal end 62, measured along the lengthwise axis 13, such that the first length 74 is equal to the second length 76. Alternatively, the center point 72 can lie anywhere between the proximal end 60 and the distal end 62. For example, the center point 72 can lie between the proximal end 60 and the distal end 62, measured along the lengthwise axis 13, such that the first length is substantially equal to the second length, the first length is greater than the second length, or the first length is less than the second length. Skilled artisans will be able to select an appropriate location for the center point 72 based on various considerations.

The distal end 62 of the plunger 16 is disposed through the opening 30 defined by the housing proximal end 24 such that the plunger second portion 68 is fully disposed in the cavity 36, the center point 72 lies adjacent the housing proximal end 24, and the plunger first portion 66 is fully disposed outside of the cavity 36. This structural arrangement provides a starting position for the plunger 16 in which the center point 72 is disposed a first distance 84 from opening 22, measured along the lengthwise axis 113.

While plunger 16 has been described as being disposed through opening 30 such that the plunger second portion 68 is disposed completely in cavity 36, center point 72 lies on housing proximal end 24, and plunger first portion 66 is disposed completely outside of cavity 36, any portion of the plunger 16 can be disposed through the opening 30 and in the cavity 36 and skilled artisans will be able to select an appropriate portion for the plunger 16 to be disposed through the opening 30 based on various considerations. Example portions of the plunger considered suitable to be disposed through an opening include the plunger first portion 66, the plunger second portion 68, a portion of the plunger first portion 66, a portion of the second portion 68, both the first portion 66 and the second portion 68, and neither of the first portion 66 or the second portion 68.

In the illustrated embodiment, the diameter 70 of the plunger 16 is less than the first diameter 42 of housing proximal portion 32. Alternatively, plunger 16 can have a diameter that is equal to, substantially equal to, or substantially less than the diameter of housing proximal portion 32 and skilled artisans will be able to select an appropriate plunger diameter based on various considerations.

While the plunger 16 has been illustrated as defining a first portion 66 having a first length 74 that is substantially equal to the second length 76 of the second portion 68, the plunger 16 can define any suitable first and second lengths and skilled artisans will be able to select appropriate first and second lengths based on various considerations. Example lengths that are considered suitable include a first length that is equal to, greater than, or less than the second length.

The plunger 16 is adapted to move axially along the lengthwise axis 13 between the starting position, a first position, and a second position. To move the plunger 16 between the starting position and the first position distal force is applied along the lengthwise axis 13 to the plunger proximal end 60. When the plunger 16 is in the first position the plunger center point 72 is disposed inside the cavity 36 distal to the housing proximal end opening 30 and a portion of the plunger first portion 66 is disposed inside the cavity 36. In this position, the center point 72 of the plunger 16 lies a second distance 86 along the lengthwise axis 13 from the cartridge distal end opening 22. The second distance 86 is less than the first distance 84. To move the plunger 16 from the first position to the starting positon, proximal force is applied to the plunger proximal end 60 along the lengthwise axis 13 such that the plunger center point 72 is disposed adjacent the opening 30. To move the plunger from the starting position to the second position, proximal force is applied to the plunger proximal end 24 along the lengthwise axis 13. In the second position, the plunger center point 72 is disposed outside the cavity 36 proximal to housing proximal end opening 30 and a portion of the plunger second portion 68 is disposed outside the cavity 36. In this position, the center point 72 lies a third distance 88 along the lengthwise axis 13 from the cartridge distal end opening 22. The third distance 88 is greater than each of the first distance 84 and the second distance 86. To move the plunger 16 from the second position to the starting position 84, distal force is applied to the plunger proximal end 24 along the lengthwise axis 13 until the plunger center point 72 moves from being disposed outside the cavity 36 to being disposed adjacent the opening 30.

In practice, when the plunger 16 is in the first position, the center point is disposed outside of the opening 22 defined on the cartridge distal end 20. As distal force is applied to the plunger proximal end 60 along the lengthwise axis 13, the plunger 16 moves from the first position towards the second position. The center point 72 that is is disposed outside the cavity 36 moves distally along the lengthwise axis 13 toward the opening 30. When the plunger 16 is advanced to the starting position, the center point 72 lies adjacent the opening 30. As distal force continues to be applied to the plunger proximal end 60 along the lengthwise axis 13, the plunger 16 advances from the starting position to the second position and the center point 72 moves distally along the lengthwise axis 13 until it is disposed in the cavity 36.

As proximal force is applied to the plunger proximal end 60 along the lengthwise axis 13, the plunger 16 moves from the second position toward the first position. The center point 72 is disposed in the cavity 36 and moves proximally along the lengthwise axis 13 toward the opening 30 defined on the housing proximal end 24. When the plunger 16 is advanced to the starting position, the center point 72 lies adjacent the opening 30. As proximal force continues to be applied to the plunger proximal end 60 along the lengthwise axis 13, the plunger 16 advances from the starting position to the first position and the center point 72 moves proximally along the lengthwise axis 13 until it is disposed outside the cavity 36.

The dynamic member 18 defines a center portion 90, a center portion diameter 92, an outer circumference 94, an outer diameter 96, a starting configuration, a first configuration and a second configuration.

In the illustrated embodiment, the dynamic member 18 is disposed in the cavity 36 defined by the housing body 28 such that the dynamic member 18 is fully disposed within the proximal portion 32 of the housing body 28.

The outer diameter 96 of the dynamic member 18 is substantially equal to the diameter 42 of the housing proximal portion 32 such that the outer circumference 94 lies adjacent the inside wall 38 of the housing body 28. In the illustrated embodiment, the outer circumference 94 is fixedly attached to the inside wall 38 of the housing body 28. Any suitable type of attachment can be used and skilled artisans will be able to select an appropriate type of attachment based on various considerations, including gluing.

While the tattoo ink mixing apparatus 10 has been illustrated as comprising a cartridge housing 14 and a dynamic member 18 as separate and distinct parts, the tattoo ink mixing apparatus 10 can comprise a cartridge housing 14 with a preformed dynamic member 18.

While the dynamic member 18 has been illustrated as being disposed in the cavity 36 within the housing proximal portion 32 and as having an outer diameter 96 that is substantially equal to the first diameter 42 of the housing proximal portion 32, the dynamic member 18 can be disposed anywhere in the cavity 36 and the dynamic member can have any suitable diameter. For example, the dynamic member 18 can be disposed in the cavity 36 within the distal portion 34 such that the dynamic member 18 has an outer diameter 96 that is equal to the second diameter 48 of the housing distal portion 34, or the dynamic member 18 can be disposed in the cavity 36 at a location within the intermediate portion 33 such that the dynamic member 18 has an outer diameter 96 that is equal to the diameter of the intermediate portion 33 at that location. Skilled artisans will be able to select appropriate locations where the dynamic member outer circumference is attached to the cartridge housing inside wall based on various considerations.

While the outer circumference 94 of the dynamic member 18 has been described as being fixedly attached to the inside wall 38 of the housing body 28, any suitable type of attachment can be made and skilled artisans will be able to select a suitable type of attachment between the dynamic member outer circumference and the cartridge housing inside wall based on various considerations. Example types of attachments considered suitable include fixed attachment, releasable attachment, and any other attachment considered suitable for a particular embodiment.

The center portion 90 of the dynamic member 18 is adapted to engage with the plunger distal end 62 and has a center portion diameter 92 that is substantially equal to the plunger diameter 70. Axial movement of the plunger distal end 62 along the lengthwise axis 13 as the plunger 16 moves between the starting position 72, the first position, and the second position causes a proportional movement in the center portion 90 of the dynamic member 18 and induces the dynamic member 18 to move between the starting configuration, the first configuration, and the second configuration.

The dynamic member 18 is adapted to move from the starting configuration to the first configuration by applying distal force to the plunger proximal end 60 along the lengthwise axis 13. As distal force is applied, the plunger 16 moves from the starting position, where the plunger center point 72 is disposed adjacent the housing proximal end opening 30, to the first position, where the plunger center point 72 is disposed in the cavity 36, and the plunger distal end 62 induces the dynamic member 18 to move from the starting configuration to the first configuration. In the first configuration 100 the plunger center point 72 is disposed in the cavity 36. To move the dynamic member 18 from the first configuration to the starting configuration, proximal force is applied to the plunger proximal end 60 along the lengthwise axis 13. As proximal force is applied, the plunger 16 moves from the first position to the starting position and the plunger distal end 62 induces the dynamic member 18 to move from the first configuration to the starting configuration. In the starting configuration, the plunger center point 72 is disposed adjacent the housing proximal end opening 30. As proximal force continues to be applied to the plunger proximal end 60 along the lengthwise axis 13, the plunger 16 moves from the starting position to the second position, and the plunger distal end 62 induces the dynamic member 18 to move from the starting configuration to the second configuration. In the second configuration, the plunger center point 72 is disposed proximal to the housing proximal end opening 30 such that the center point 72 is disposed outside the cavity 36. To move the dynamic member 18 from the second configuration to the starting configuration, distal force is applied to the plunger proximal end 60 along the lengthwise axis 13. As distal force is applied, the plunger 16 moves from the second position to the starting position and the plunger distal end 62 induces the dynamic member 18 to move from the second configuration to the starting configuration.

In practice, the cartridge distal end 20 is optionally disposed in an ink reservoir containing tattoo ink (not shown) such that the opening 22 and a portion of the housing distal portion 34 are disposed in the ink. When proximal force is applied to the plunger proximal end 60 along the lengthwise axis 13, the plunger distal end 62 moves proximally along the lengthwise axis 13 and engages with the center portion 90 of the dynamic member 18. This engagement moves the dynamic member 18 from the starting configuration or the first configuration to the second configuration. This change in configurations causes suction force to occur in the housing cavity 36 and causes ink to be drawn up through the opening 22 and into the cavity 36. When distal force is applied to the plunger proximal end 60 along the lengthwise axis 13, the plunger distal end 62 moves distally along the lengthwise axis 13 and engages with the center portion 90 of the dynamic member 18. This engagement with the center portion 90 moves the dynamic member 18 from the starting configuration or the second configuration to the first configuration. This change in configurations causes an expulsion force to occur in the housing cavity 36 and causes ink to be expelled out of the opening 22.

Figure 2:
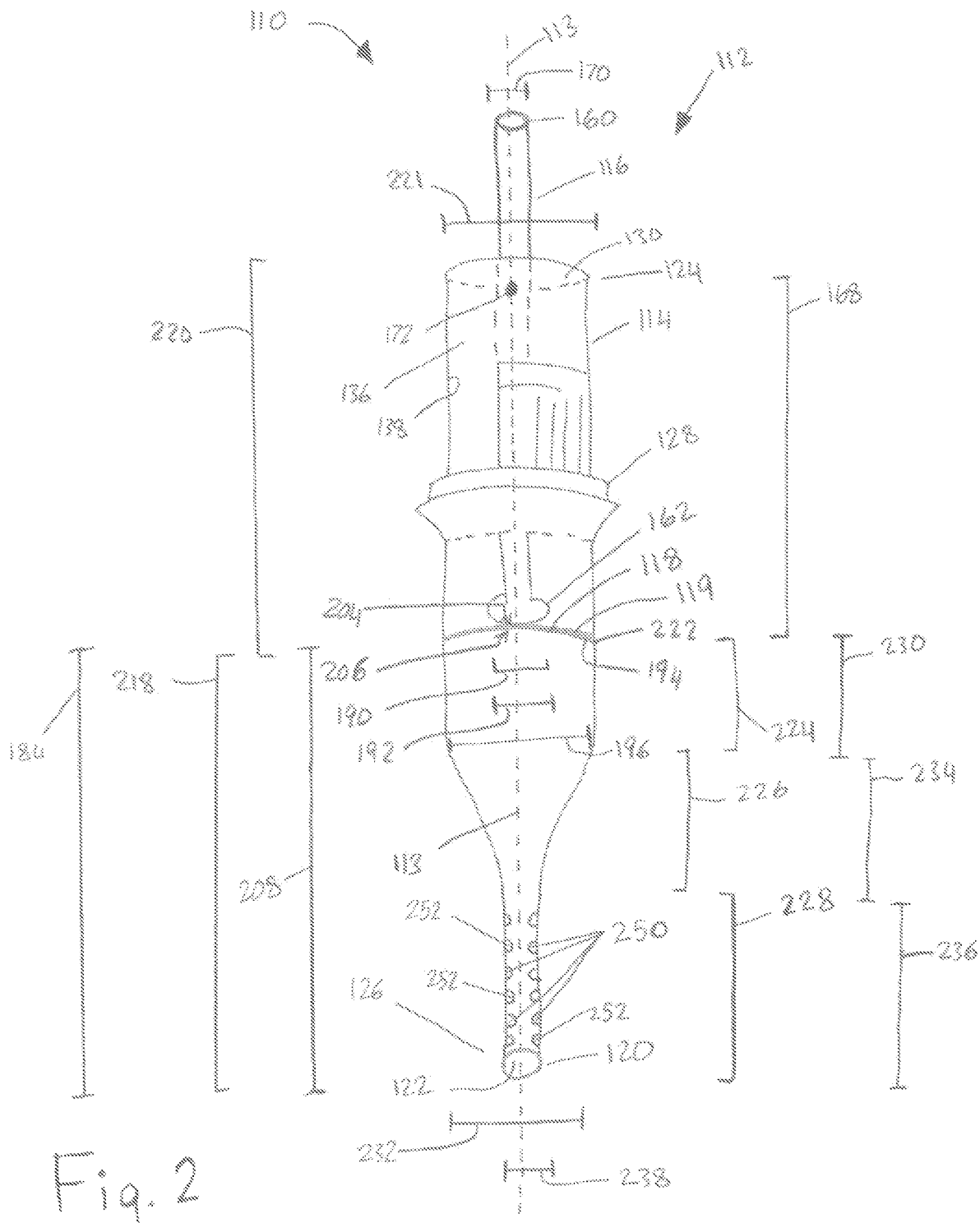
FIG. 2 is a perspective view of another example tattoo ink mixing apparatus with a dynamic member in a starting position.
Figure 3:
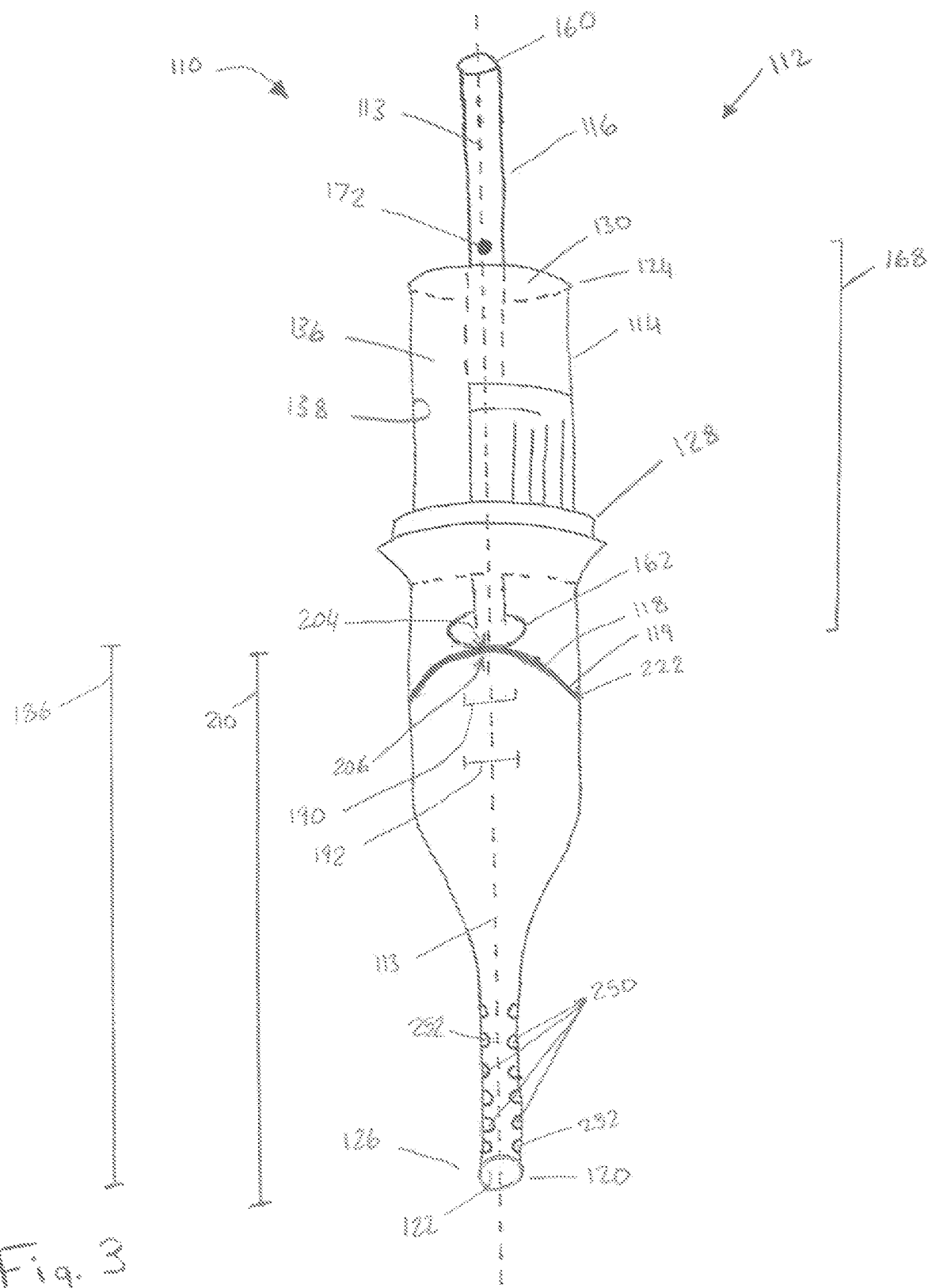
FIG. 3 is a perspective view of the tattoo ink mixing of FIG. 2 with the dynamic member in a first configuration.
Figure 4:
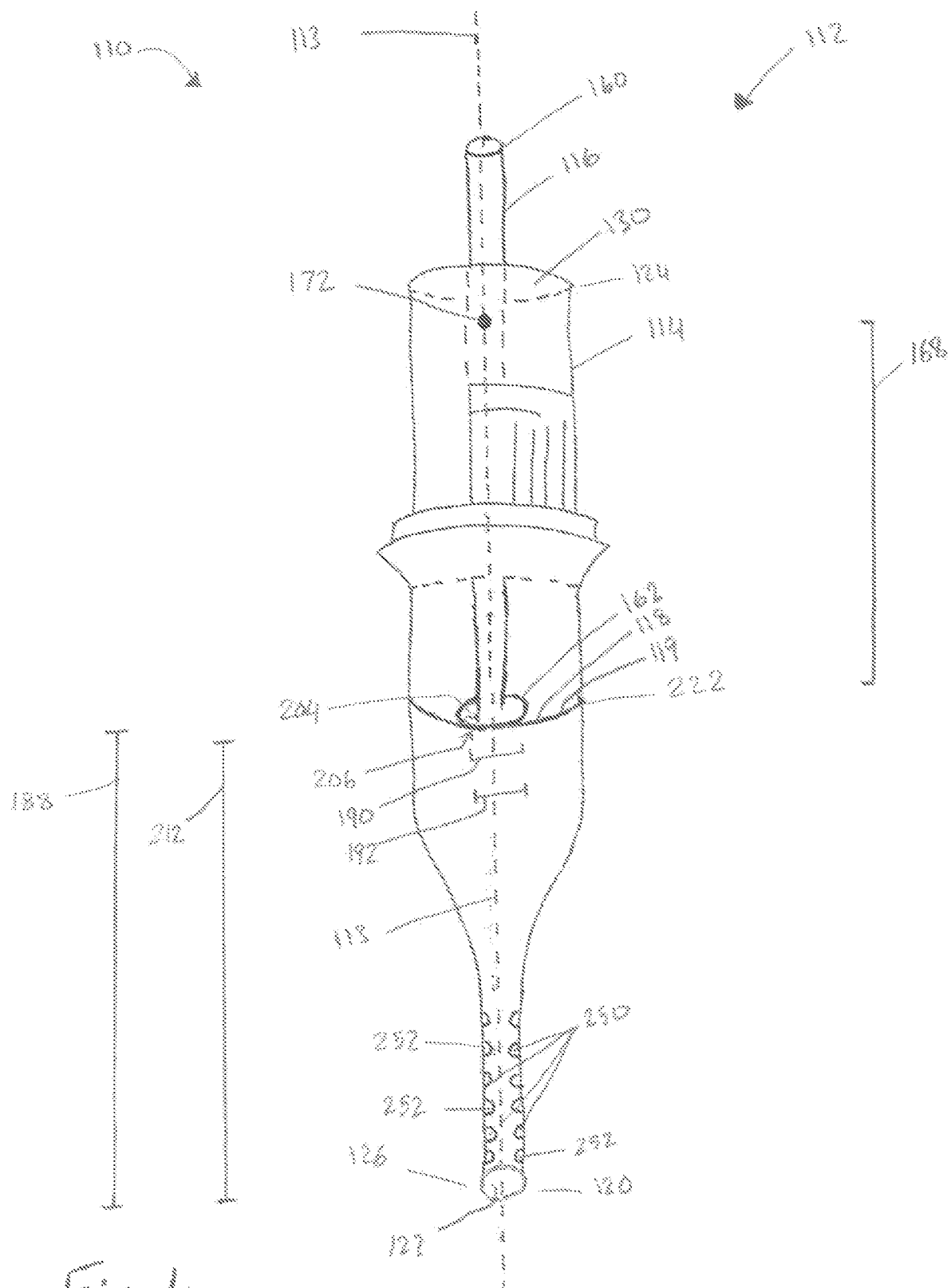
FIG. 4 is a perspective view of the tattoo ink mixing of FIG. 2 with the dynamic member in a second configuration.

FIGS. 2, 3, and 4 illustrate another example embodiment of a tattoo ink mixing apparatus 110. Tattoo ink mixing apparatus 110 is similar to the tattoo ink mixing apparatus 10 illustrated in FIG. 1 and described above, except as detailed below. Reference numbers in FIGS. 2, 3, and 4 refer to the same structural element or feature referenced by the same numbers in FIG. 1, offset by 100. Thus, the tattoo ink mixing apparatus 110 comprises a cartridge 112 having a lengthwise axis 113, a cartridge housing 114, a plunger 116, a dynamic member 118, and a cartridge distal end 120 defining an opening 122.

In this embodiment, the cavity 136 defines an inside wall 138, a cavity mixing chamber 218, and a cavity proximal chamber 220. The inside wall 138 extends from the opening 130 defined by the housing proximal end 124 to the opening 122 defined on the cartridge distal end 120. The cavity proximal chamber 220 extends from the opening 130 to a first location 222 between the housing proximal end 124 and the housing distal end 126. The cavity proximal chamber 220 has a first diameter 221 and is adapted to receive the second portion 168 of the plunger 116 such that the plunger center point 172 lies adjacent the opening 130.

The cavity mixing chamber 218 extends from the first location 222 to the opening 122 defined on the cartridge distal end 120. The cavity mixing chamber 218 comprises a proximal portion 224, an intermediate portion 226, and a distal portion 228. The proximal portion 224 extends from the first location 222 to the intermediate portion 226 and has a proximal portion length 230 and a proximal portion diameter 232. The intermediate portion 226 tapers from the proximal portion 224 to the distal portion 228 and has an intermediate portion length 234. The distal portion 228 extends from the intermediate portion 226 to the opening 122 and has a distal portion length 236 and a distal portion diameter 238. In the illustrated embodiment, the proximal portion diameter 232 is equal to the first diameter 221 of the cavity proximal portion 220 and is greater than the distal portion diameter 238.

In this embodiment, the distal portion 228 of the cavity mixing chamber 218 defines a plurality of passageways 250 that individually provide fluid communication between the cavity mixing chamber 218 and an environment external to the cartridge housing 114. While the illustrated embodiment includes a plurality of passageways 250, it is noted that only one or two passageways can be included on a housing distal portion according to a particular embodiment. Indeed, any suitable number of passageways can be included. Furthermore, the passageways on a housing distal portion according to a particular embodiment can have any suitable size, shape, configuration, arrangement, and location. The number, size, shape, configuration, arrangement, and location of passageways included on a housing distal portion according to a particular embodiment can be selected by a skilled artisan based on various considerations. The inventor(s) have determined that a plurality of passageways that comprises opposably positioned series of passageways is suitable for a cartridge intended to be used to mix tattoo ink in an ink reservoir.

As illustrated in FIGS. 3 and 4, and as will be described in more detail herein, the cavity mixing chamber 218 is adapted to receive tattoo ink (not shown). As the dynamic member 118 moves from the second configuration to the first configuration, the internal pressure of the cavity mixing chamber 218 decreases to a level below the pressure of the environment external to the cartridge housing 114. This causes ink to be drawn through the opening 122 defined on the cartridge distal end 120 and/or one or more passageway 252 of the plurality of passageways 250 and into the distal portion 228 of the cavity mixing chamber 218. The ink then travels proximally through the distal portion 228 towards the intermediate portion 226 and the proximal portion 224 of the cavity mixing chamber 218. As the dynamic member 118 continues to move toward the first configuration, the ink travels proximally through the intermediate portion 226 and into the proximal portion 224 of the cavity mixing chamber 218. When the dynamic member 118 is in the first configuration, the cavity mixing chamber 218 is substantially full of ink. As the dynamic member 118 moves from the first configuration to the second configuration, the internal pressure of the cavity mixing chamber 218 increases to a level greater than the pressure of the environment external to the cartridge housing 114. This causes ink to travel distally from the proximal portion 224 to the distal portion 228, passing through the intermediate portion 226. As the dynamic member 118 continues to move toward the second configuration, the ink is expelled through the opening 122 and/or one or more passageway 252 of the plurality of passageways 250. When the dynamic member 118 is in the second configuration, the cavity mixing chamber 218 is substantially empty of ink.

As illustrated in FIGS. 3 and 4, the distal end 162 of the plunger 116 is fixedly attached to the first side 204 of the center portion 190 of the dynamic member 118. When the plunger 116 is in the starting position, the plunger distal end 162 lies adjacent the first location 222 and the plunger center point 172 lies adjacent the opening 130 defined on the housing proximal end 124. In the starting position, the plunger distal end 162 is disposed a first distance 184 from the opening 122 defined on the cartridge distal end 120, measured along the lengthwise axis 113. When the plunger 116 is in the first position, the plunger distal end 162 lies distal to the first location 222 and is disposed in the proximal portion 224 of the cavity mixing chamber 218. The plunger distal end 162 is disposed a second distance 186 from the opening 122, measured along the lengthwise axis 113. In the first position, the plunger center point 172 lies distal to the opening 130 and is disposed inside the proximal chamber 220 of the cavity 136. When the plunger 116 is in the second position, the plunger distal end 162 lies proximal to the first location 222 and is disposed in the proximal chamber 220 of the cavity 136. The plunger distal end 162 is disposed a third distance 188 from the opening 122, measured along the lengthwise axis 113. In the second position, the plunger center point 172 lies proximal to the opening 130 and is disposed outside of the proximal chamber 220 of the cavity 136.

In this embodiment, the dynamic member 118 defines a center portion 190, an outer circumference 194, an outer diameter 196, a starting configuration, a first configuration and a second configuration.

The center portion 190 of the dynamic member 118 has a first side 204, a second side 206, and a center portion diameter 192. The diameter 192 of the center portion 190 is substantially equal to the diameter 170 of the plunger 116. The first side 204 is fixedly attached to the distal end 162 of the plunger 116 and the second side 206 is in communication with the proximal portion 224 of the cavity mixing chamber 218. Any suitable type of attachment can be used and skilled artisans will be able to select an appropriate type of attachment based on various considerations. Example suitable types of attachments include gluing or any other type of attachment considered suitable for a particular embodiment.

While the first side 204 of the center portion 190 of the dynamic member 118 has been described as being fixedly attached to the plunger distal end 162, any suitable type of attachment can be made and skilled artisans will be able to select a suitable type of attachment between the center portion and the plunger distal end based on various considerations, including releasable attachment and any other attachment considered suitable for a particular embodiment.

The dynamic member 118 is disposed in the cavity 136 such that the dynamic member 118 lies adjacent the first location 222. In the illustrated embodiment, the dynamic member 118 functions as a sealing member and comprises an elastic membrane 119 that has an outer diameter 196. In the illustrated embodiment, the outer diameter 196 of the dynamic member 118 is substantially equal to the first diameter 221 of the cavity proximal chamber 220. The outer circumference 194 of the dynamic member 118 lies adjacent the inside wall 138 of the cavity 136 and is fixedly attached to the inside wall 138 at the first location 222. Such a structural configuration results in the dynamic member 118 forming a tight seal between the cavity mixing chamber 218 and the cavity proximal chamber 220 such that tattoo ink is not able to travel from the proximal portion 224 of the cavity mixing chamber 218 to the cavity proximal chamber 220.

As illustrated in FIGS. 3 and 4, the dynamic member 118 is adapted to move between a starting configuration, a first configuration, and a second configuration. In the starting configuration, the plunger is in the starting position and the center portion 190 of the dynamic member 118 is disposed adjacent the first location 222. Each of the center portion 190 and the outer circumference 194 extends a first distance 208 from the opening 122 defined on the cartridge distal end 120, measured along the lengthwise axis 113. The first distance 208 is equal to the first distance 184 of the distal end 162 of the plunger 116. When distal force is applied to the plunger proximal end 160 along the lengthwise axis 113, the plunger distal end 162 pushes the center portion 190 of the dynamic member 118 distally until the center portion 190 is disposed a second distance 210 from the opening 122, measured along the lengthwise axis 113. The second distance 210 of the center portion 190 is equal to the second distance 186 of the plunger distal end 162. In the second configuration, the center portion 190 is disposed distal to the outer circumference 194 of the dynamic member 118 and distal to the first location 222 such that the center portion 190 is disposed in the proximal portion 224 of the cavity mixing chamber 218. When proximal force is applied to the plunger proximal end 160 along the lengthwise axis 113, the plunger distal end 162 pulls the center portion 190 of the dynamic member 118 proximally until the center portion 190 is disposed a third distance 212 from the opening 122, measured along the lengthwise axis 113. The third distance 212 of the center portion 190 is equal to the third distance 188 of the plunger distal end 162. In the third configuration, the center portion 190 is disposed proximal to the outer circumference 194 of the dynamic member 118 and proximal to the first location 222 such that the center portion 190 is disposed in the proximal chamber 220 of the cavity 136.

In practice, the cartridge distal end 120 is optionally disposed in an ink reservoir containing tattoo ink (not shown) such that a portion of the distal portion 228 of the cavity mixing chamber 218, the opening 22 defined on the cartridge distal end 120, and at least one passageway 252 of the plurality of passageways 250 are disposed in the ink. When proximal force is applied to the plunger proximal end 160 along the lengthwise axis 113, the dynamic member 118 moves from the second configuration to the first configuration. During this transition from the second configuration to the first configuration, the plunger distal end 162 and the center portion 190 of the dynamic member 118 move proximally along the lengthwise axis 113 until the plunger distal end 162 and the center portion 190 are disposed in the proximal chamber 220 of the cavity 136. As the center portion 190 moves proximally towards the second distance 210, the internal pressure inside the cavity mixing chamber 218 decreases to a level less than the pressure of the environment external to the cartridge housing 114. This causes ink to be drawn through the opening 122 defined on the cartridge distal end 120 and/or one or more passageways 252 of the plurality of passageways 250 and into the distal portion 228 of the cavity mixing chamber 218. The ink then travels proximally through the distal portion 228 and into the intermediate portion 226 and proximal portion 224 of the cavity mixing chamber 218. When the dynamic member 118 is in the first configuration, the cavity mixing chamber 218 is substantially full of ink.

When distal force is applied to the plunger proximal end 160 along the lengthwise axis 113, the dynamic member 118 moves from the first configuration to the second configuration. During this transition from the first configuration to the second configuration, the plunger distal end 162 and the center portion 190 of the dynamic member 118 move distally along the lengthwise axis 113 until the plunger distal end 162 and the center portion 190 are disposed in the proximal portion 224 of the cavity mixing chamber 218. As the center portion 190 moves distally towards the first distance 208, the internal pressure inside the cavity mixing chamber 218 increases to a level greater than the pressure of the environment external to the cartridge housing 114. As the dynamic member 118 moves from the second configuration to the first configuration, the internal pressure of the cavity mixing chamber 218 drops below the pressure of the environment external to the cartridge housing 114. This causes the ink to travel distally through the proximal portion 224, into the intermediate portion 226, and into the distal portion 228. As the dynamic member 118 continues to move toward the second configuration, the ink is expelled through one or more passageways 252 of the plurality of passageways 250 and/or the opening 122 defined on the cartridge distal end 120. When the dynamic member 118 is in the second configuration, the cavity mixing chamber 218 is substantially empty of ink. The repeated movement of the dynamic member 118 between the first configuration and the second configuration causes ink to be continuously drawn and expelled through the opening 122 and/or one or more passageways 252 of the plurality of passageways 250 causing the ink to be stirred.

Figure 5:
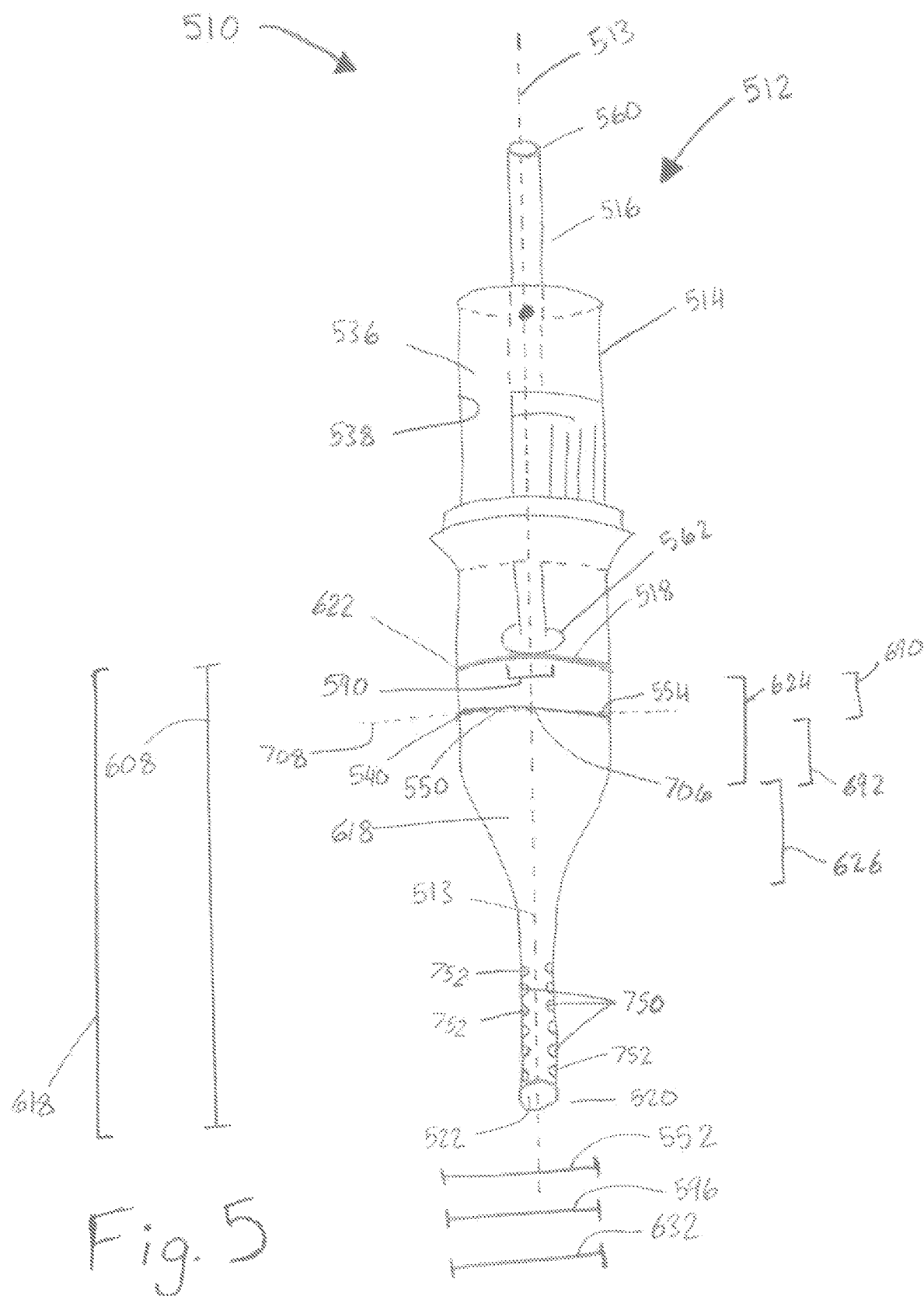
FIG. 5 is a perspective view of another example tattoo ink mixing apparatus with a dynamic member in a starting position.
Figure 6:
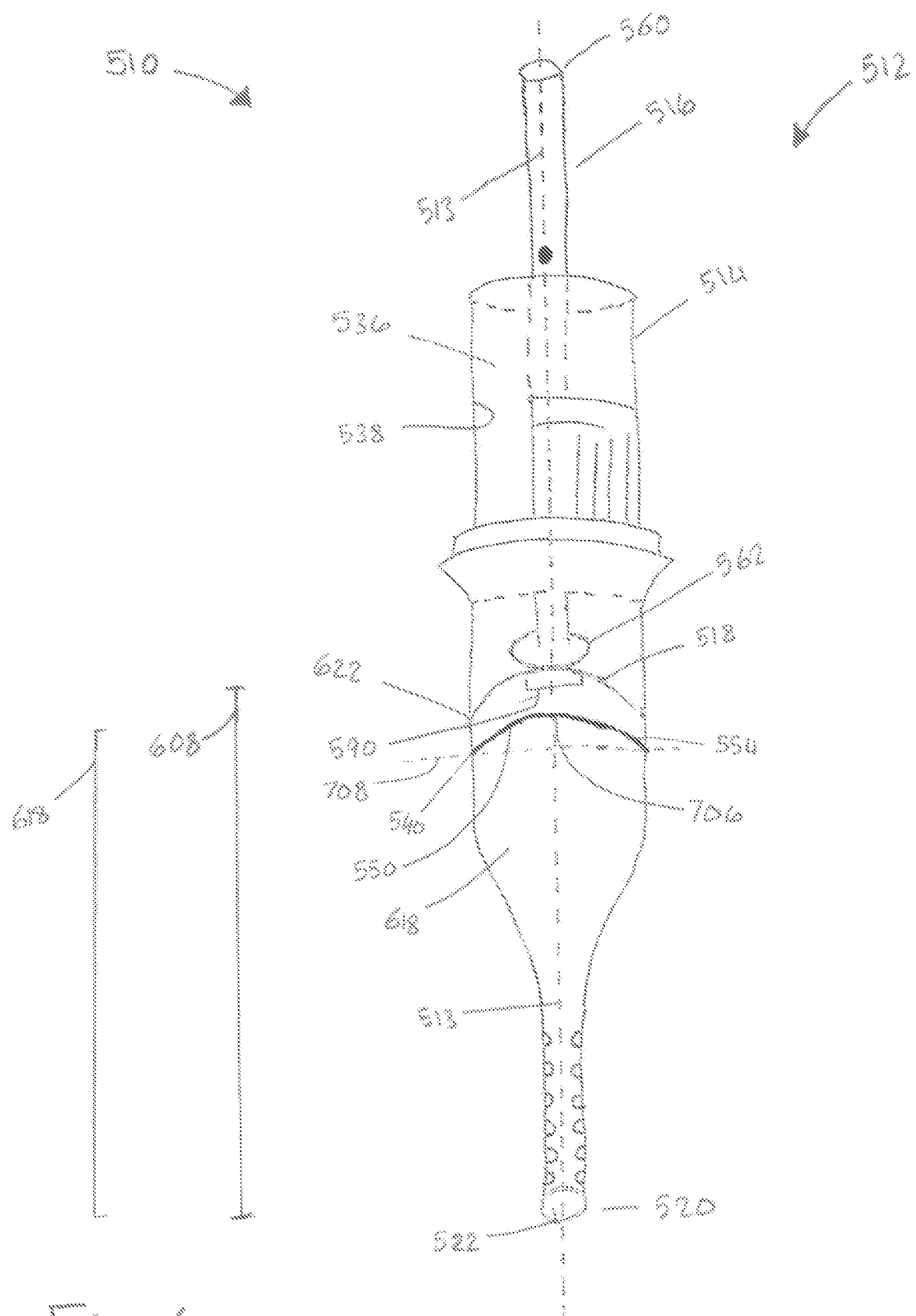
FIG. 6 is a perspective view of the tattoo ink mixing of FIG. 5 with the dynamic member in a first configuration.
Figure 7:
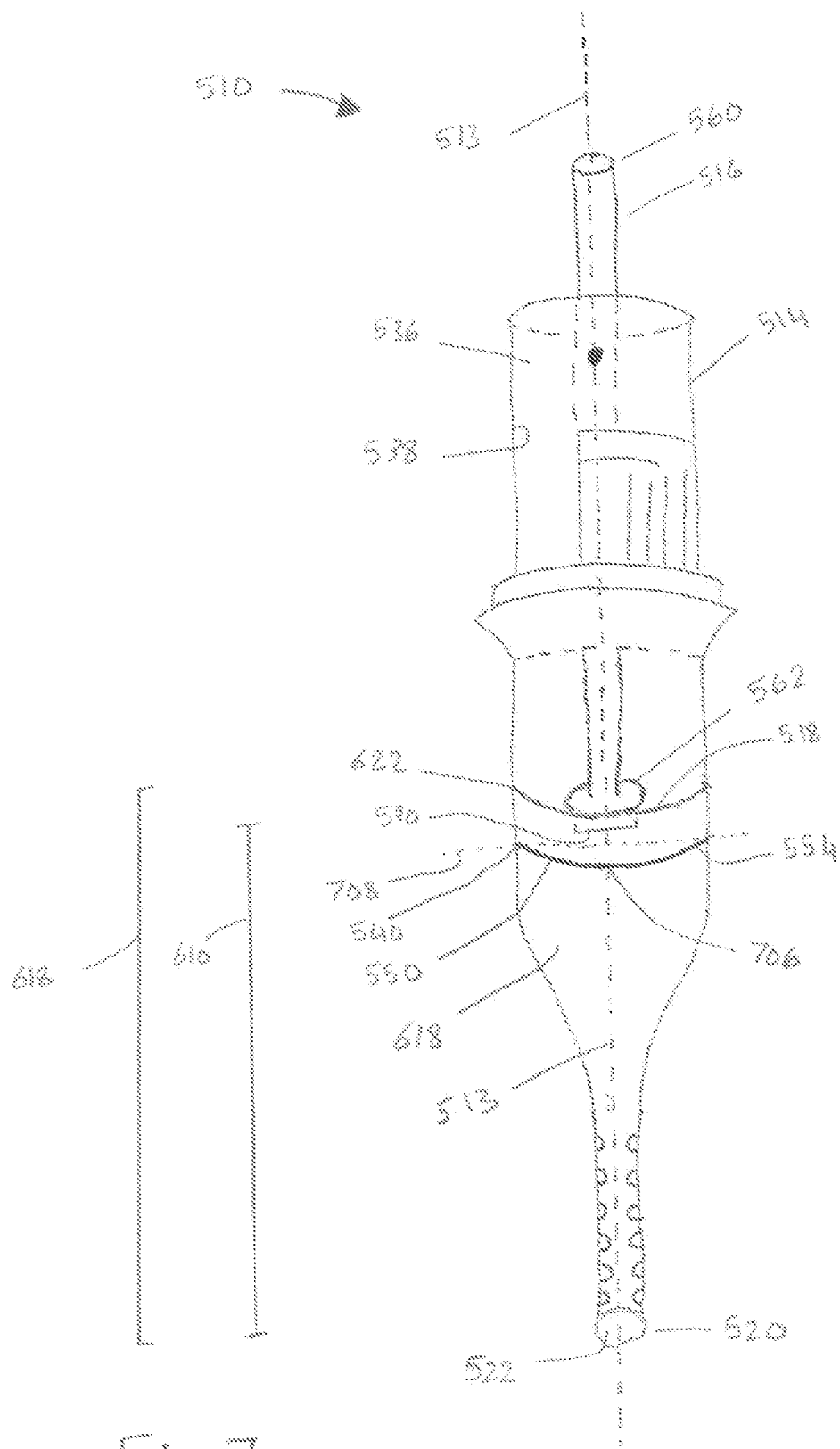
FIG. 7 is a perspective view of the tattoo ink mixing of FIG. 5 with the dynamic member in a second configuration.

While the cartridge 112 has been described as having a dynamic member 118 that forms a tight seal between the cavity mixing chamber 218 and the cavity proximal chamber 220 to prevent ink from traveling from the proximal portion 224 of the cavity mixing chamber 218 to the cavity proximal chamber 220, any suitable sealant can be used and skilled artisans will be able to select a suitable sealant based on various considerations. For example, FIGS. 5, 6, and 7 illustrate another example embodiment of the tattoo ink mixing apparatus 510. Tattoo ink mixing apparatus 510 is similar to the tattoo ink mixing apparatus 110 illustrated in FIG. 2 and described above, except as detailed below. Reference numbers in FIGS. 5, 6, and 7 refer to the same structural element or feature referenced by the same numbers in FIG. 2, offset by 400. Thus, the tattoo ink mixing apparatus 510 comprises a cartridge 512 having a lengthwise axis 513, a cartridge housing 514, a plunger 516, a dynamic member 518, and a cartridge distal end 520 defining an opening 522.

In this embodiment, the tattoo ink mixing apparatus 510 comprises a cartridge 512 that further defines a sealing membrane 550. The sealing membrane 550 is disposed distal to the dynamic member 518 in the proximal portion 624 of the cavity mixing chamber 618. The sealing membrane 550 has a diameter 552 that is substantially equal to each of the outer diameter 596 of the dynamic member 518 and the diameter 632 of the proximal portion 624 of the cavity mixing chamber 618. The sealing membrane 550 has a circumference 554 that is fixedly attached to the inside wall 538 of the cavity 536 at a location 540 between the first location 622 and the intermediate portion 626. The sealing membrane 550 forms a tight seal between a first portion 690 of the proximal portion 624 that is proximal to the sealing membrane 550 and a second portion 692 of the proximal portion 624 that is distal to the sealing membrane 550. The sealing membrane 550 prevents ink from traveling from the second portion 692 to the first portion 690. The first portion 690 extends from the dynamic member 518 to the sealing membrane 550 and is sealed proximally by the dynamic member 518, distally by the sealing membrane 550, and circumferentially by the cartridge housing 514.

As illustrated in FIGS. 6 and 7, the sealing membrane 550 defines a starting configuration, a first configuration, and a second configuration. In the starting configuration, the dynamic member 518 is in the starting configuration and the center 706 of the sealing membrane 550 and the circumference 554 of the sealing member 550 lie on a plane 708 that is orthogonal to the lengthwise axis 513. In the first configuration, the dynamic member 518 is in the first configuration and the center 706 of the sealing membrane 550 lies distal to the circumference 554 of the sealing member 550 such that the center 706 is disposed in the second portion 692 of the proximal portion 624 of the cavity mixing chamber 618. In the second configuration, the dynamic member 518 is in the second configuration and the center 706 of the sealing membrane 550 lies proximal to the circumference 554 of the sealing member 550 such that the center 706 is disposed in the first portion 690 of the proximal portion 624 of the cavity mixing chamber 618.

As the dynamic member 518 moves from the first configuration to the second configuration, the internal pressure in the first portion 690 of the proximal portion 624 of the cavity mixing chamber 618 decreases to a level less than the environment external to the cartridge housing 514. This causes the sealing membrane 550 to move from the second configuration to the first configuration. This, in turn, causes the internal pressure in the second portion 692 of the proximal portion 624 of the cavity mixing chamber 618 to decrease to a level less than the pressure of the environment external to the cartridge housing 514 causing tattoo ink to be drawn into the cavity 536 through one or more passageways 752 of the plurality of passageways 750 and/or the opening 522 defined on the cartridge distal end 520.

As the dynamic member 518 moves from the second configuration to the first configuration, the internal pressure in the first portion 690 of the proximal portion 624 of the cavity mixing chamber 618 increases to a level greater than the pressure of the environment external to the cartridge housing 514. This causes the sealing membrane 550 to move from the first configuration to the second configuration. This, in turn, causes the internal pressure in the second portion 692 of the proximal portion 624 of the cavity mixing chamber 618 to increase to a level greater than the pressure of the environment external to the cartridge housing 514 causing tattoo ink to be expelled out of the cavity 536 through one or more passageways 752 of the plurality of passageways 750 and/or the opening 522 defined on the cartridge distal end 520.

While cartridge 512 has been described as including a single sealing membrane 550, any suitable number of sealing membranes can be used and a skilled artisan will be able to select an appropriate number based on various considerations. Example numbers of sealing membranes considered suitable include one, more than one, a plurality, two, three, or any other number of sealing membranes considered suitable for a particular embodiment.

Figure 8:
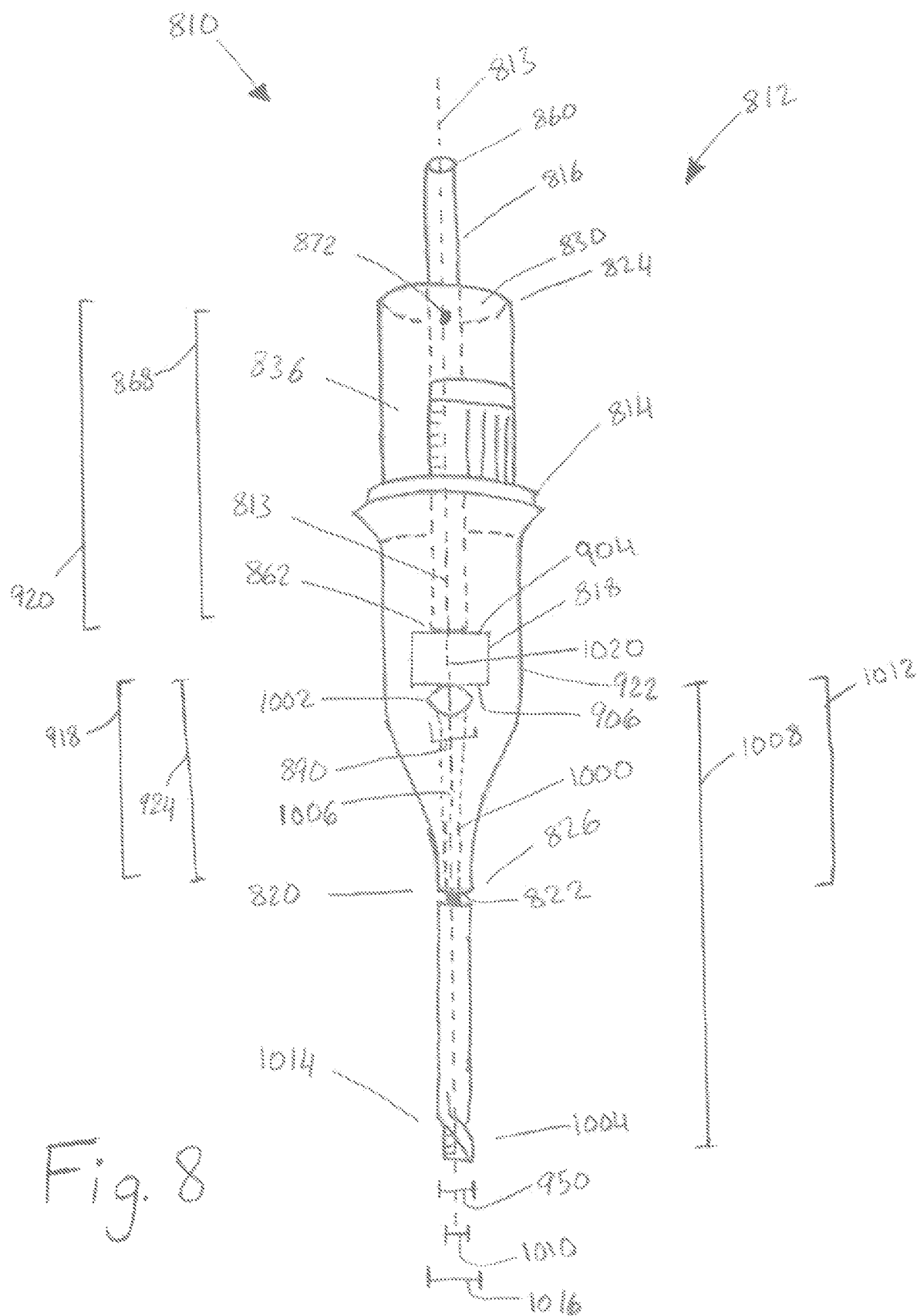
FIG. 8 is a perspective view of another example tattoo ink mixing apparatus.

FIG. 8 illustrates another example embodiment of a tattoo ink mixing apparatus 810. Tattoo ink mixing apparatus 810 is similar to the tattoo ink mixing apparatus 10 illustrated in FIG. 1 and described above, except as detailed below. Reference numbers in FIG. 8 refer to the same structural element or feature referenced by the same numbers in FIG. 1, offset by 800. Thus, the tattoo ink mixing apparatus 810 comprises a cartridge 812 having a lengthwise axis 813, a cartridge housing 814, a plunger 816, a dynamic member 818, and a cartridge distal end 820 defining an opening 822.

In this embodiment, the cartridge 812 further defines a mixing tip 1000. The mixing tip 1000 has a proximal end 1004, a distal end 1006, and an elongate body 1006 extending from the proximal end 1004 to the distal end 1006. The elongate body 1006 has a diameter 1010 and a length 1008 measured along the lengthwise axis 813. The distal end 1006 defines a structural feature 1014 that has a diameter 1016. The diameter 1016 of the structural feature 1014 is greater than the diameter 1010 of the elongate body 1006 of the mixing tip 1000. Alternatively, the structural feature 1014 can have a diameter 1016 that is less than, equal to, or substantially equal to the diameter 1010 of the elongate body 1006.

The mixing tip 1000 can have a distal end 1006 defining any structural feature 1014 considered suitable for a particular embodiment and skilled artisans will be able to select a suitable structural feature based on various considerations. Example structural features that are considered suitable include a blade.

The elongate body 1006 has a diameter 1010 that is less than the diameter 950 of the opening 822 defined on the cartridge distal end 820. In the illustrated embodiment, the proximal end 1004 is inserted through the opening 822 and is disposed in the cavity mixing chamber 918 such that a portion 1012 of the elongate body 1006 of the mixing tip 1000 is disposed in the cavity mixing chamber 918. The elongate body 1006 defines a length 1008 that extends from the proximal end 1002 of the mixing tip 1000 to the distal end 1004 of the mixing tip 1000.

In this embodiment, the cavity 836 defines a cavity mixing chamber 918 and a cavity proximal chamber 920. The cavity mixing chamber 918 extends from a first location 922 between the housing proximal end 824 and the housing distal end 826 to the opening 822 defined on the cartridge distal end 820. The mixing chamber 918 defines a length 924 that is less than the length 1008 of the elongate body 1006 of the mixing tip 1000. The cavity mixing chamber 918 is adapted to receive the proximal end 1002 of the mixing tip 1000 and a portion 1012 of the elongate body 1006 of the mixing tip 1000 such that the proximal end 1002 and the portion 1012 of the elongate member 1006 are disposed in the cavity mixing chamber 918.

The cavity proximal chamber 920 extends from the opening 830 defined on the housing proximal end 824 to the first location 922. The cavity proximal chamber 920 has a first diameter 921 and is adapted to receive the second portion 868 of the plunger 816.

In this embodiment, the center portion 890 of the dynamic member 818 comprises a gearing 1020 that converts the linear motion of the plunger 816 into rotational motion for the mixing tip 1000, i.e. the gearing 1020 transforms axial motion into radial motion. In this embodiment, the gearing 1020 has a first side 904 and a second side 906. The first side 904 is adapted to receive the distal end 862 of the plunger 816. The second side 906 is adapted to receive the proximal end 1002 of the mixing tip 1000.

The gearing 1020 can comprise any machine or part that transforms axial motion of the plunger 816 along the lengthwise axis 813 into radial motion for the mixing tip 1000 along the lengthwise axis 813. The radial motion causes the proximal end 1002, the elongate body 1006, and the distal end 1006 with the structural feature 1014 to rotate about the lengthwise axis 813. The direction of rotation depends on the type of gearing used and skilled artisans will be able to select an appropriate gearing to define a direction of rotation based on various considerations. Example directions of rotations that are considered suitable include clockwise, counter-clockwise, and both clockwise and counter-clockwise. For example, the gearing can be adapted to transform the proximal and distal linear motion of the plunger 816 to clockwise rotation, counter-clockwise rotation, and/or both clockwise and counter-clockwise rotation.

Any gearing that transforms axial motion into radial motion can be used and skilled artisans will be able to select an appropriate gearing based on various considerations. Example gearings that are considered suitable include barrel cam, crank, or any other gearing considered suitable for a particular embodiment.

Figure 9:
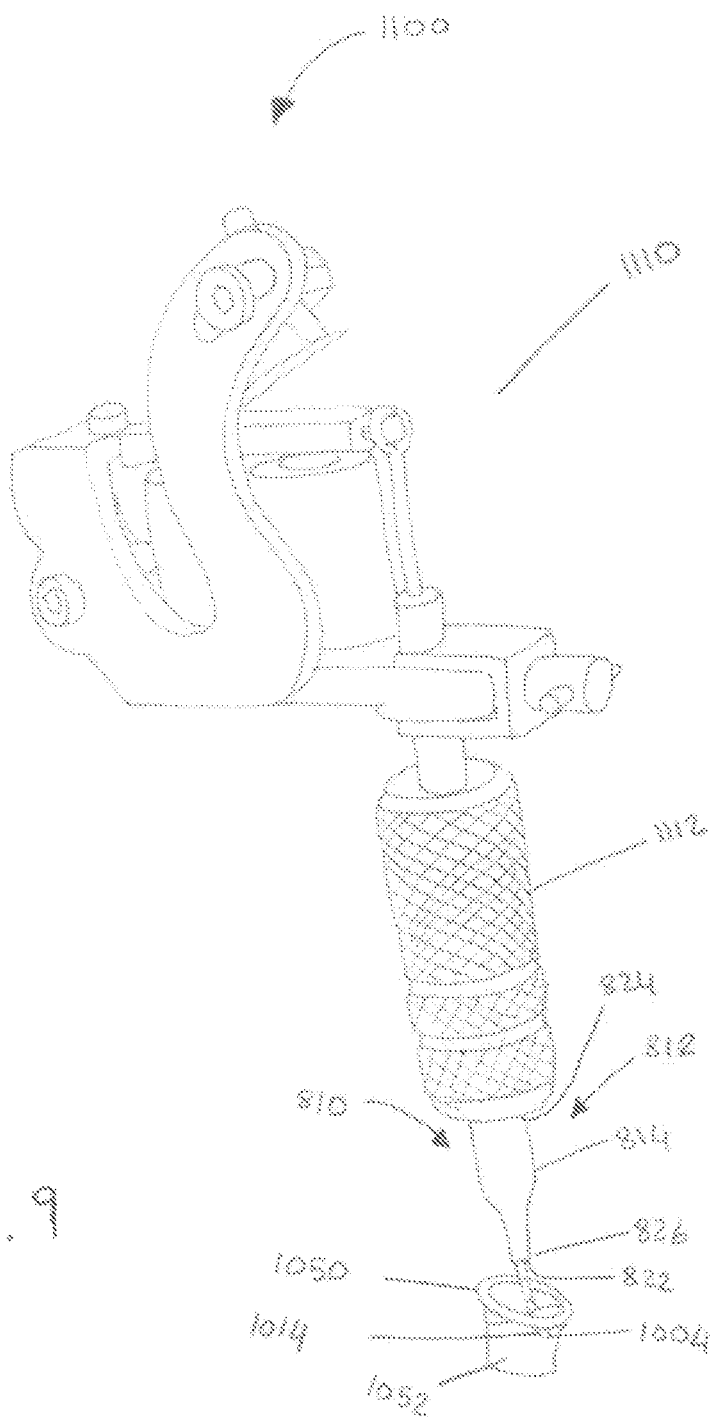
FIG. 9 is a perspective view of an example tattoo machine system including the tattoo ink mixing apparatus illustrated in FIG. 8.

FIG. 9 illustrates an example tattoo machine system 1100 useful for the application of tattoos and for mixing tattoo ink. The tattoo machine system 1100 comprises the tattoo ink mixing apparatus 810 illustrated FIG. 8, a tattoo machine 1110, and a cartridge grip 1112. The tattoo machine system 1100 can also optionally include an ink reservoir 1052. The tattoo ink mixing apparatus 810 comprises all the elements illustrated in FIG. 8 and described above. Thus, the tattoo ink mixing apparatus 810 comprises a cartridge 812 having a lengthwise axis 813, a cartridge housing 814, a plunger 816, a dynamic member 818, and a cartridge distal end 820 defining an opening 822.

The tattoo machine system 1100 can include any suitable tattoo machine 1110 and skilled artisans will be able to select an appropriate tattoo machine based on various considerations.

The tattoo machine system 1100 can include any suitable cartridge grip 1112 and skilled artisans will be able to select an appropriate cartridge grip based on various considerations.

The tattoo machine system 1100 can optionally include any ink reservoir 1052 and skilled artisans will be able to select an appropriate ink reservoir based on various considerations. The inclusion of an ink reservoir 1052 is completely optional and skilled artisans will be able to select whether or not to include an ink reservoir 1052 in a tattoo machine system 1100.

While tattoo machine system 1100 has been described as comprising the tattoo ink mixing apparatus 810 illustrated in FIG. 8, the tattoo machine system 1100 can comprise any tattoo ink mixing apparatus. Skilled artisans will be able to select an appropriate tattoo ink mixing apparatus to be included in the tattoo machine system 1100 based on various considerations. For example, the tattoo machine system 1100 can comprise the tattoo ink mixing apparatus 10 illustrated in FIG. 1, the tattoo ink mixing apparatus 110 illustrated in FIGS. 2, 3, and 4, the tattoo ink mixing apparatus 510 illustrated in FIGS. 5, 6, and 7, or any other tattoo ink mixing apparatus considered suitable for a particular embodiment.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A tattoo ink mixing apparatus having a lengthwise axis and comprising:
    a housing having a housing proximal end, a housing distal end, a housing body extending from the housing proximal end to the housing distal end, the housing proximal end defining a housing proximal end opening, the housing distal end defining a housing distal end opening, the housing body defining a cavity extending from the housing proximal end opening to the housing distal end opening, the cavity defining a cavity proximal chamber and a cavity mixing chamber, the cavity proximal chamber extending from the housing proximal end opening to a first location between the housing proximal end and the housing distal end, the cavity mixing chamber extending from the first location to the housing distal end opening;
    a plunger having a plunger proximal end, a plunger distal end, and a plunger elongate body extending from the plunger proximal end to the plunger distal end, the plunger distal end disposed through the housing proximal end opening and in the cavity, the plunger adapted to move between a plunger first position in which the plunger distal end is disposed a first distance from the housing distal end and a second position in which the plunger distal end is disposed a second distance from the housing distal end, the first distance being greater than the second distance as measured along the lengthwise axis;
    a mixing tip having a mixing tip proximal end, a mixing tip distal end, and a mixing tip elongate body extending from the mixing tip proximal end to the mixing tip distal end, the mixing tip elongate body having a mixing tip elongate body diameter, the mixing tip proximal end disposed through the housing distal end opening and in the cavity, the mixing tip distal end defining a structural feature, the structural feature having a structural feature diameter that is greater than the mixing tip elongate body diameter; and
    a gearing adapted to convert linear motion of the plunger into rotational motion of the mixing tip.

2. The tattoo ink mixing apparatus of claim 1, wherein the structural feature is a blade.

3. The tattoo ink mixing apparatus of claim 1, wherein a portion of the structural feature extends along a helical path.

4. The tattoo ink mixing apparatus of claim 1, wherein the gearing is a crank.

5. The tattoo ink mixing apparatus of claim 1, wherein the gearing is a barrel cam.

6. The tattoo ink mixing apparatus of claim 1, wherein the plunger has a diameter that is less than a first diameter of a housing proximal portion, the housing proximal portion extending from the housing proximal end to a housing intermediate portion, the housing intermediate portion extending from the housing proximal portion to a housing distal portion, the housing distal portion extending from the housing intermediate portion to the housing distal end.

7. The tattoo ink mixing apparatus of claim 1, wherein a plunger center point is disposed adjacent the housing proximal end opening when in a plunger starting configuration.

8. The tattoo ink mixing apparatus of claim 1, wherein a plunger center point is disposed proximal to the housing proximal end opening when in a plunger starting configuration.

9. The tattoo ink mixing apparatus of claim 1, wherein the plunger has a diameter that is substantially the same as a first diameter of a housing proximal portion, the housing proximal portion extending from the housing proximal end to a housing intermediate portion, the housing intermediate portion extending from the housing proximal portion to a housing distal portion, the housing distal portion extending from the housing intermediate portion to the housing distal end.

10. The tattoo ink mixing apparatus of claim 1, wherein the plunger has a diameter that is less than a first diameter of a housing proximal portion, the housing proximal portion extending from the housing proximal end to a housing intermediate portion, the housing intermediate portion extending from the housing proximal portion to a housing distal portion, the housing distal portion extending from the housing intermediate portion to the housing distal end.

11. The tattoo ink mixing apparatus claim 1, wherein the mixing tip elongate body diameter is less than the housing distal end opening.

12. The tattoo ink mixing apparatus of claim 1, wherein the housing has a housing proximal portion, a housing intermediate portion, and a housing distal portion, the housing proximal portion extending from the housing proximal end to the housing intermediate portion, the housing intermediate portion extending from the housing proximal portion to the housing distal portion, the housing distal portion extending from the housing intermediate portion to the housing distal end, the housing intermediate portion having a diameter that is greater than the diameter of the housing proximal portion.

13. The tattoo ink mixing apparatus of claim 1, wherein the housing has a housing proximal portion, a housing intermediate portion, and a housing distal portion, the housing proximal portion extending from the housing proximal end to the housing intermediate portion, the housing intermediate portion extending from the housing proximal portion to the housing distal portion, the housing distal portion extending from the housing intermediate portion to the housing distal end the housing intermediate portion and the housing distal portion having substantially the same diameter.

14. The tattoo ink mixing apparatus of claim 1, wherein the gearing has a first side and a second side.

15. The tattoo ink mixing apparatus of claim 14, wherein the first side is adapted to receive the plunger distal end.

16. The tattoo ink mixing apparatus of claim 14, wherein the second side is adapted to receive the mixing tip proximal end.

17. The tattoo ink mixing apparatus of claim 14, wherein the first side is adapted to receive the plunger distal end; and
   the second side is adapted to receive the mixing tip proximal end.

18. The tattoo ink mixing apparatus of claim 1, wherein the cavity proximal chamber having a cavity proximal chamber length along the lengthwise axis, the cavity mixing chamber having a cavity mixing chamber length along the lengthwise axis, the cavity mixing chamber length is greater than the cavity proximal chamber length along the lengthwise axis.

19. A tattoo ink mixing apparatus having a lengthwise axis and comprising:
   a housing having a housing proximal end, a housing distal end, a housing body extending from the housing proximal mal end to the housing distal end, the housing proximal end defining a housing proximal end opening, the housing distal end defining a housing distal end opening, the housing body defining a cavity extending from the housing proximal end opening to the housing distal end opening, the cavity defining a cavity proximal chamber and a cavity mixing chamber, the cavity proximal chamber extending from the housing proximal end opening to a first location between the housing proximal end and the housing distal end, the cavity mixing chamber extending from the first location to the housing distal end opening;
   a plunger having a plunger proximal end, a plunger distal end, and a plunger elongate body extending from the plunger proximal end to the plunger distal end, the plunger distal end disposed through the housing proximal end opening and in the cavity, the plunger adapted to move between a plunger first position in which the plunger distal end is disposed a first distance from the housing distal end and a second position in which the plunger distal end is disposed a second distance from the housing distal end, the first distance being greater than the second distance as measured along the lengthwise axis;
   a mixing tip having a mixing tip proximal end, a mixing tip distal end, and a mixing tip elongate body extending from the mixing tip proximal end to the mixing tip distal end, the mixing tip elongate body having a mixing tip elongate body diameter, the mixing tip proximal end disposed through the housing distal end opening and in the cavity, the mixing tip distal end defining a structural feature, the structural feature having a structural feature diameter that is less than the mixing tip elongate body diameter; and
   a gearing adapted to convert linear motion of the plunger into rotational motion of the mixing tip.

20. A tattoo ink mixing apparatus having a lengthwise axis and comprising:
   a housing having a housing proximal end, a housing distal end, a housing body extending from the housing proximal end to the housing distal end, the housing proximal end defining a housing proximal end opening, the housing distal end defining a housing distal end opening, the housing body defining a cavity extending from the housing proximal end opening to the housing distal end opening, the cavity defining a cavity proximal chamber and a cavity mixing chamber, the cavity proximal chamber extending from the housing proximal end opening to a first location between the housing proximal end and the housing distal end, the cavity mixing chamber extending from the first location to the housing distal end opening;
   a plunger having a plunger proximal end, a plunger distal end, and a plunger elongate body extending from the plunger proximal end to the plunger distal end, the plunger distal end disposed through the housing proximal end opening and in the cavity, the plunger adapted to move between a plunger first position in which the plunger distal end is disposed a first distance from the housing distal end and a second position in which the plunger distal end is disposed a second distance from the housing distal end, the first distance being greater than the second distance as measured along the lengthwise axis;
   a mixing tip having a mixing tip proximal end, a mixing tip distal end, and a mixing tip elongate body extending from the mixing tip proximal end to the mixing tip distal end, the mixing tip elongate body having a mixing tip elongate body diameter, the mixing tip proximal end disposed through the housing distal end opening and in the cavity, the mixing tip distal end defining a structural feature, the structural feature having a structural feature diameter that is equal to the mixing tip elongate body diameter; and a gearing adapted to convert linear motion of the plunger into rotational motion of the mixing tip.

* * * * *